(12) United States Patent
Drochner et al.

(10) Patent No.: US 9,427,328 B2
(45) Date of Patent: Aug. 30, 2016

(54) INTERBODY IMPLANT SYSTEM AND METHOD

(71) Applicant: Warsaw Orthopedic, Inc., Warsaw, IN (US)

(72) Inventors: Thomas E. Drochner, Memphis, TN (US); Jonathan E. Blackwell, Arlington, TN (US); Cristian A. Capote, Memphis, TN (US); Anthony J. Melkent, Germantown, TN (US); Michael J. Merves, Collierville, TN (US); Bret M. Wilfong, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 64 days.

(21) Appl. No.: 14/203,125

(22) Filed: Mar. 10, 2014

(65) Prior Publication Data
US 2015/0250607 A1 Sep. 10, 2015

(51) Int. Cl.
*A61F 2/44* (2006.01)
*A61F 2/30* (2006.01)

(52) U.S. Cl.
CPC ............. *A61F 2/4455* (2013.01); *A61F 2/447* (2013.01); *A61F 2002/305* (2013.01); *A61F 2002/3008* (2013.01); *A61F 2002/30014* (2013.01); *A61F 2002/30062* (2013.01); *A61F 2002/30131* (2013.01); *A61F 2002/30133* (2013.01); *A61F 2002/30747* (2013.01); *A61F 2002/30772* (2013.01); *A61F 2002/30836* (2013.01); *A61F 2002/30909* (2013.01); *A61F 2002/4475* (2013.01); *A61F 2002/4495* (2013.01); *A61F 2310/00017* (2013.01); *A61F 2310/00023* (2013.01); *A61F 2310/00029* (2013.01); *A61F 2310/00293* (2013.01)

(58) Field of Classification Search
CPC ........... A61F 2/442; A61F 2002/4435; A61F 2002/4445; A61F 2/4455
USPC ............................................. 623/17.11–17.16
See application file for complete search history.

(56) References Cited

U.S. PATENT DOCUMENTS

| | | |
|---|---|---|
| 3,061,080 A | 10/1962 | Stephen |
| 3,315,402 A | 4/1967 | Scott et al. |
| 4,328,904 A | 5/1982 | Iverson |
| 5,025,947 A | 6/1991 | Leone |
| 5,259,501 A | 11/1993 | Withers et al. |
| 5,676,990 A | 10/1997 | Wawrzynski |
| 5,964,533 A | 10/1999 | Ziglar |
| 6,656,514 B1 | 12/2003 | Tubbs |
| 7,591,388 B2 | 9/2009 | Amormino |
| 8,292,960 B2 | 10/2012 | Kleiner |
| 8,524,265 B2 | 9/2013 | McKay |
| 8,585,766 B2 | 11/2013 | Ulrich |
| 2001/0035414 A1 | 11/2001 | Tyree |
| 2005/0252923 A1 | 11/2005 | Woolf |
| 2005/0263523 A1 | 12/2005 | Moss |
| 2007/0012701 A1 | 1/2007 | Amormino |
| 2008/0172127 A1* | 7/2008 | Perez-Cruet .......... A61F 2/4611 623/17.16 |
| 2010/0215718 A1 | 8/2010 | Swords |
| 2011/0190888 A1* | 8/2011 | Bertele et al. ............. 623/17.11 |
| 2012/0310354 A1* | 12/2012 | Ullrich, Jr. ............ A61F 2/4465 623/17.16 |
| 2013/0110238 A1* | 5/2013 | Lindemann ......... A61F 2/30744 623/17.12 |

* cited by examiner

*Primary Examiner* — Ellen C Hammond
*Assistant Examiner* — Christina Negrellirodrigue

(57) ABSTRACT

An interbody endcap comprises at least one member configured for connection with an interbody implant. The at least one member has a thickness that permits bone growth therethrough and a uniform surface configuration that resists and/or prevents egress of bone graft from a cavity of the interbody implant. Systems and methods are disclosed.

19 Claims, 10 Drawing Sheets

INTERBODY IMPLANT SYSTEM AND METHOD

TECHNICAL FIELD

The present disclosure generally relates to medical devices for the treatment of musculoskeletal disorders, and more particularly to a surgical system that includes an interbody implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminedomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, an interbody endcap is disclosed. The interbody endcap comprises at least one member configured for connection with an interbody implant. The at least one member has a thickness that permits bone growth therethrough and a uniform surface configuration that resists and/or prevents egress of bone graft from a cavity of the interbody implant. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
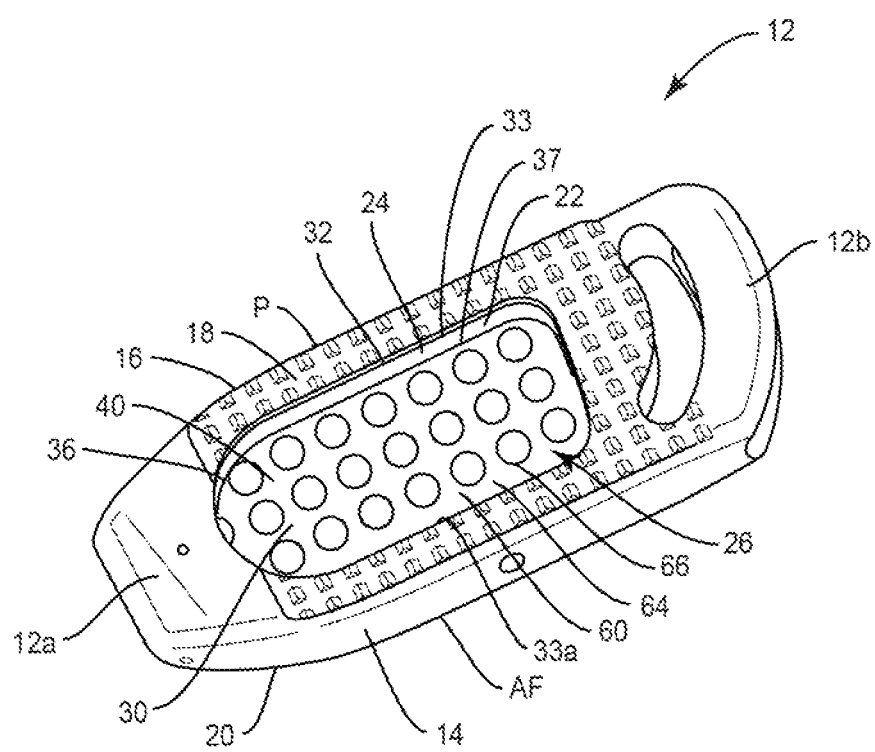
FIG. 1 is a perspective view of components of one embodiment of a spinal implant in accordance with the principles of the present disclosure.
Figure 2:
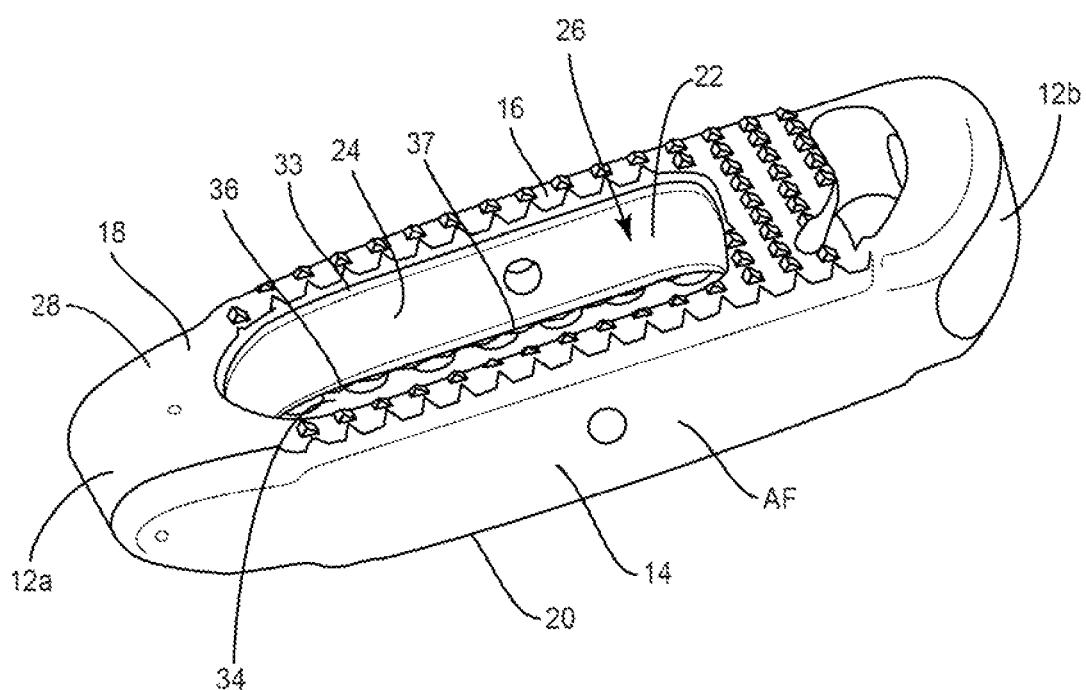
FIG. 2 is a perspective view of the components shown in FIG. 1.

The exemplary embodiments of the surgical system and related methods of use disclosed are discussed in terms of medical devices for the treatment of musculoskeletal disorders and more particularly, in terms of a surgical system that includes an interbody implant and a method for treating a spine. In some embodiments, the surgical system of the present disclosure provides an interbody implant that can be employed with a method, such as, for example, anterior lumbar interbody fusion (ALIF), oblique lateral interbody fusion (OLIF) and/or a direct lateral interbody fusion (DLIF).

In one embodiment, the present system includes an interbody implant having a large surface area. In one embodiment, the interbody implant includes a large footprint configured to contact one or both apophyseal rings adjacent an intervertebral space. In one embodiment, the interbody implant includes a large graft window. In some embodiments, the interbody implant includes a device configured to maintain bone graft material within the graft window during insertion into an intervertebral disc space in a configuration to prevent voids of the graft in the graft window. In one embodiment, the interbody implant includes a mesh cap configured for disposal with a graft window to contain bone graft until the interbody implant is implanted into an intervertebral disc space. In one embodiment, the mesh cap is configured to allow bone growth through openings in the mesh.

In one embodiment, the present system includes an interbody implant having a mesh cap configured to snap fit with the interbody implant and contain bone graft packed into apertures in a center of the interbody implant. In one embodiment, a thin recess is disposed around a top and/or a bottom graft opening in the interbody implant. In one embodiment, the mesh cap includes openings sized to keep bone graft from exiting out of the interbody implant while allowing bone to grow through.

In one embodiment, the interbody implant includes two mesh caps configured to snap together such that the caps are independent from the interbody implant. In some embodiments, a first mesh cap is disposed with the interbody implant and graft material is placed into the center of the interbody implant. In one embodiment, a second mesh cap is disposed with the interbody implant and connected with the first mesh cap to enclose the graft material.

In one embodiment, the mesh cap is flexible such that the cap is configured to fit into a graft window. In one embodiment, the flexible mesh cap straightens to fit into a recess disposed about the graft window. In one embodiment, the interbody implant includes a slot disposed on at least one side of the interbody implant and is configured to receive the mesh cap. In one embodiment, the slot is configured to facilitate the mesh cap sliding into engagement with the interbody implant. In one embodiment, the interbody implant includes at least one recess configured to facilitate sliding of the mesh cap for insertion with a top position and dropped into a final position.

In one embodiment, the interbody implant includes a built in, integrally connected and/or monolithically formed mesh cap on a first side. In one embodiment, the interbody implant includes a recess on a second side configured to receive an additional mesh cap. In one embodiment, the additional mesh cap is configured to engage the built in mesh cap, such as, for example, with a snap fit.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc hemiation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alliteratively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-8, there are illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, an interbody implant, at a surgical site within a body of a patient, for example, a section of a spine. In some embodiments, system 10 may be employed with surgical procedures, such as, for example, corpectomy and discectomy, which include fusion and/or fixation treatments that employ implants to restore the mechanical support function of vertebrae.

Figure 6:
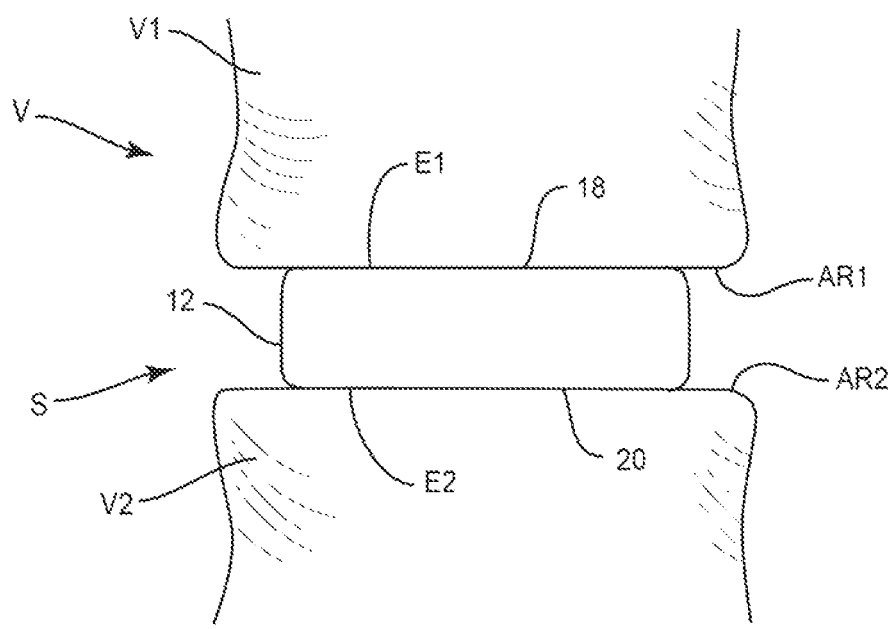
FIG. 6 is a side view of components of one embodiment of a spinal implant in accordance with the principles of the present disclosure disposed with vertebrae.
Figure 7:
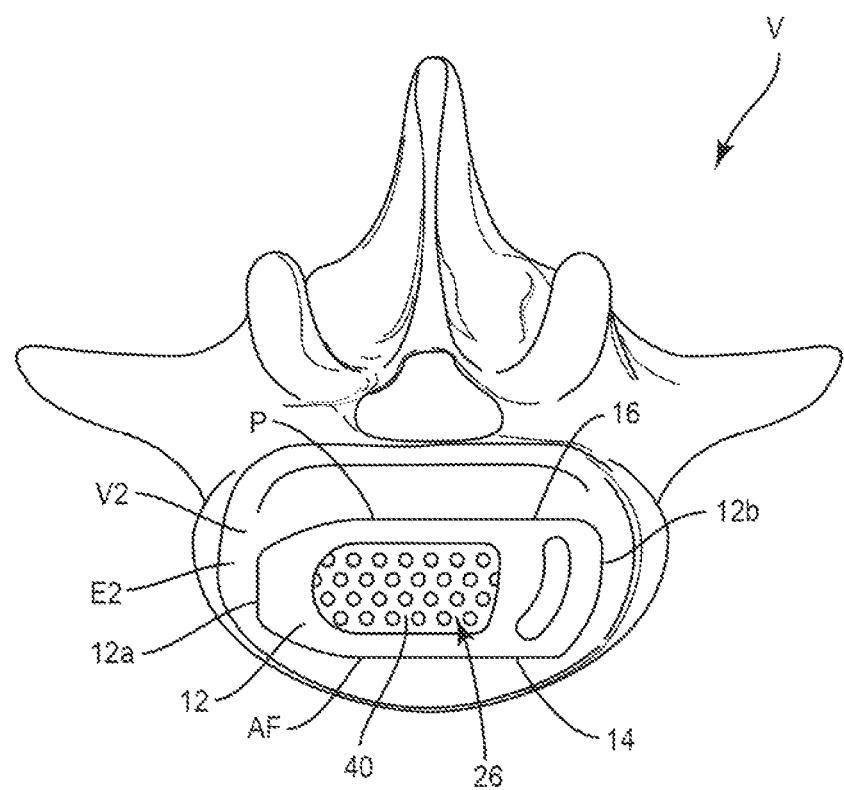
FIG. 7 is an axial view of the components and vertebrae shown in FIG. 6.

System 10 includes a spinal implant, such as, for example, an interbody implant 12. Interbody implant 12 includes an implant body that extends between a front end 12a and a rear end 12b. Interbody implant 12 also extends between a first surface, such as, for example, an anterior surface 14 defining an anterior face AF and a second surface, such as, for example, a posterior surface 16 defining a posterior face P. Interbody implant 12 includes a vertebral engaging surface 18 oriented to contact vertebral tissue, such as, for example, all or only a portion of an apophyseal ring AR1 of a vertebral endplate surface E1 of a vertebral body V1, as shown in FIGS. 6 and 7. In some embodiments, surface 18 is substantially planar.

Interbody implant 12 includes a vertebral engaging surface 20 oriented to contact vertebral tissue, such as, for example, all or only a portion of an apophyseal ring AR2 of a vertebral endplate surface E2 of a vertebral body V2. In some embodiments, surface 20 is substantially planar. In some embodiments, surface 18 and/or surface 20 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone.

Interbody implant 12 includes an inner surface 22 that defines a wall 24. Wall 24 defines a cavity 26 configured to receive bone graft, an agent and/or other selected materials, as described herein, for employment in a fixation, fusion and/or other treatment, as described herein. In some embodiments, the cross-sectional geometry of interbody implant 12 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In one embodiment, the agent may include therapeutic polynucleotides or polypeptides and bone growth promoting material, which can be packed within cavity 26. The agent may also include biologically active agents, for example, biologically active agents coated onto the exterior and/or interior of implant 12 and/or applied thereto for gradual release such as by blending in a bioresorbable polymer that releases the biologically active agent or agents in an appropriate time dependent fashion as the polymer degrades within the patient. Suitable biologically active agents include, for example, BMP and cytokines. Implant 12 includes an outer surface 28. In some embodiments, outer surface 28 may be textured, rough, porous, semi-porous, dimpled and/or polished.

Surface 18 defines an opening 30 disposed in communication with cavity 26 and wall 24. Opening 30 is oriented to provide access to cavity 26 through surface 18. In one embodiment, opening 30 facilitates delivery and/or introduction of an agent, bone graft and/or other selected materials into cavity 26. In some embodiments, opening 30 may have various configurations, such as, for example, circular, oval, oblong, triangular, rectangular, polygonal, planar side(s), arcuate side(s), irregular, uniform, non-uniform, offset, staggered, variable, U-shape, kidney bean shape and/or multiple openings.

Surface 22 defines a recess 32 disposed adjacent surface 18 and configured for disposal of an interbody endcap, as discussed herein. Recess 32 extends about opening 30 and includes linear and arcuate portions. In some embodiments, the surface defining recess 32 may be textured, rough, porous, semi-porous, dimpled and/or polished to facilitate connection with the interbody endcap. Surface 22 includes locking flanges 33, 33a that define a portion of recess 32 and extend into opening 30. Locking flanges 33, 33a engage the interbody endcap to retain the interbody endcap with surface 22 and within recess 32 in a fixed and/or locked orientation, as discussed herein.

Surface 20 defines an opening 34 that communicates with cavity 26. Opening 34 is configured to provide access to cavity 26. In one embodiment, opening 34 facilitates delivery and/or introduction of an agent, bone graft and/or other selected materials into cavity 26. In some embodiments, opening 34 may have various configurations, such as, for example, circular, oval, oblong, triangular, rectangular, polygonal, planar side(s), arcuate side(s), irregular, uniform, non-uniform, offset, staggered, variable, U-shape, kidney bean shape and/or multiple openings.

Surface 22 defines a recess 36 disposed adjacent surface 20 and configured for disposal of an interbody endcap, as discussed herein. Recess 36 extends about opening 34 and includes linear and arcuate portions. In some embodiments, the surface defining recess 36 may be textured, rough, porous, semi-porous, dimpled and/or polished to facilitate connection with the interbody endcap. Surface 22 includes locking flanges 37, 37a that define a portion of recess 36 and extend into opening 34. Locking flanges 37, 37a engage the interbody endcap to retain the interbody endcap with surface 22 and within recess 36 in a fixed and/or locked orientation, as discussed herein.

Figure 4:
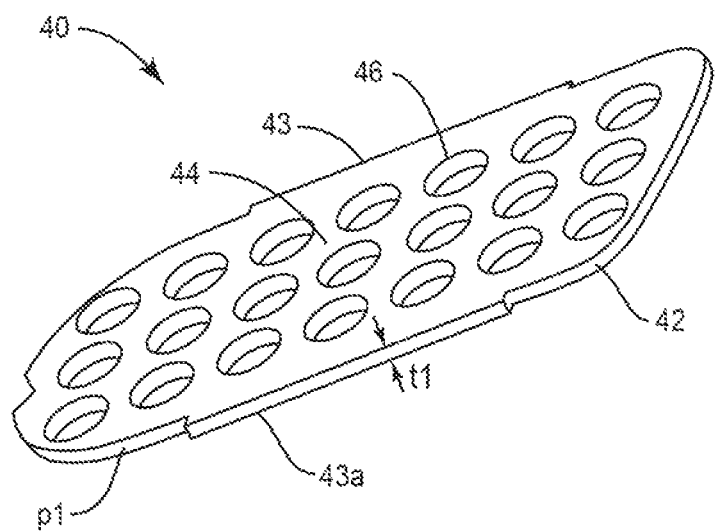
FIG. 4 is a perspective view of a component of one embodiment of a spinal implant in accordance with the principles of the present disclosure.

Implant 12 includes an interbody endcap that comprises a member 40, as shown in FIG. 4, configured for connection and mating engagement with the surface that defines recess 32. In some embodiments, endcap 40 has various configurations, such as, for example, oval-shaped, arcuate, crescent, horseshoe, hook-shaped, rectangular and/or those geometric alternatives described herein. Endcap 40 includes a wall 42 having a thickness t1 configured to permit bone growth therethough. In some embodiments, al or a portion of thickness t1 may alternately be non-uniform, staggered, offset, undulating and/or tapered.

Wall 42 includes a perimeter p1 disposed about endcap 40. Perimeter p1 includes linear and arcuate portions. Perimeter p1 includes flanges 43, 43a configured for disposal within recess 32. Flange 33 engages flange 43 and flange 33a engages flange 43a to retain endcap 40 with surface 22 and within recess 32 in a fixed and/or locked orientation.

Endcap 40 includes a surface 44 having a uniform configuration that resists and/or prevents egress of bone graft, agents and/or other selected materials from cavity 26 in an integrally connected and/or assembled configuration with the implant body of implant 12, for example, during introduction, delivery and/or insertion of implant 12 with tissue and/or to contain bone graft, agents and/or other selected materials packed with cavity 26 until implant 12 is implanted with tissue, as described herein. In one embodiment, surface 44 includes a series of selectively configured and dimensioned openings 46. Openings 46 comprise a plurality of apertures, each opening 46 having a circular configuration. In some embodiments, openings 46 comprise a series of sets of openings including a plurality of rows oriented in selected alignment. In one embodiment, each row of apertures comprises a set of openings. In some embodiments, surface 44 comprises a uniform mesh configuration. In some embodiments, surface 44 comprises a uniform configuration of perforations.

In some embodiments, surface 44 includes a series of selectively configured and dimensioned sets of openings. For example, the series of openings may include rows and/or columns that are selectively aligned, staggered, offset, angled and/or spaced apart. In some embodiments, each set of openings includes a plurality of alternately configured and dimensioned openings. For example, each set of openings can include one or more circular apertures, polygonal apertures, undulating apertures, non-uniform shaped apertures, polygonal slots, oval slots, barrel shaped apertures, undulating slots and/or non-uniform shaped slots. In one embodiment, as shown in FIG. 5, surface 44 includes a repeating series of a row R1 that includes a set of alliterating recessed circular apertures 48a and substantially trapezoidal slots 48b having at least one undulating side, a second row R2 that includes a set of alternating slots 48c having undulating sides and non-uniform apertures 48d, a row R3 that includes a set of alternating apertures 48a and non-uniform slots 48e and a row R4 having large non-uniform slots 48f and small non-uniform slots 48g.

Figure 5:
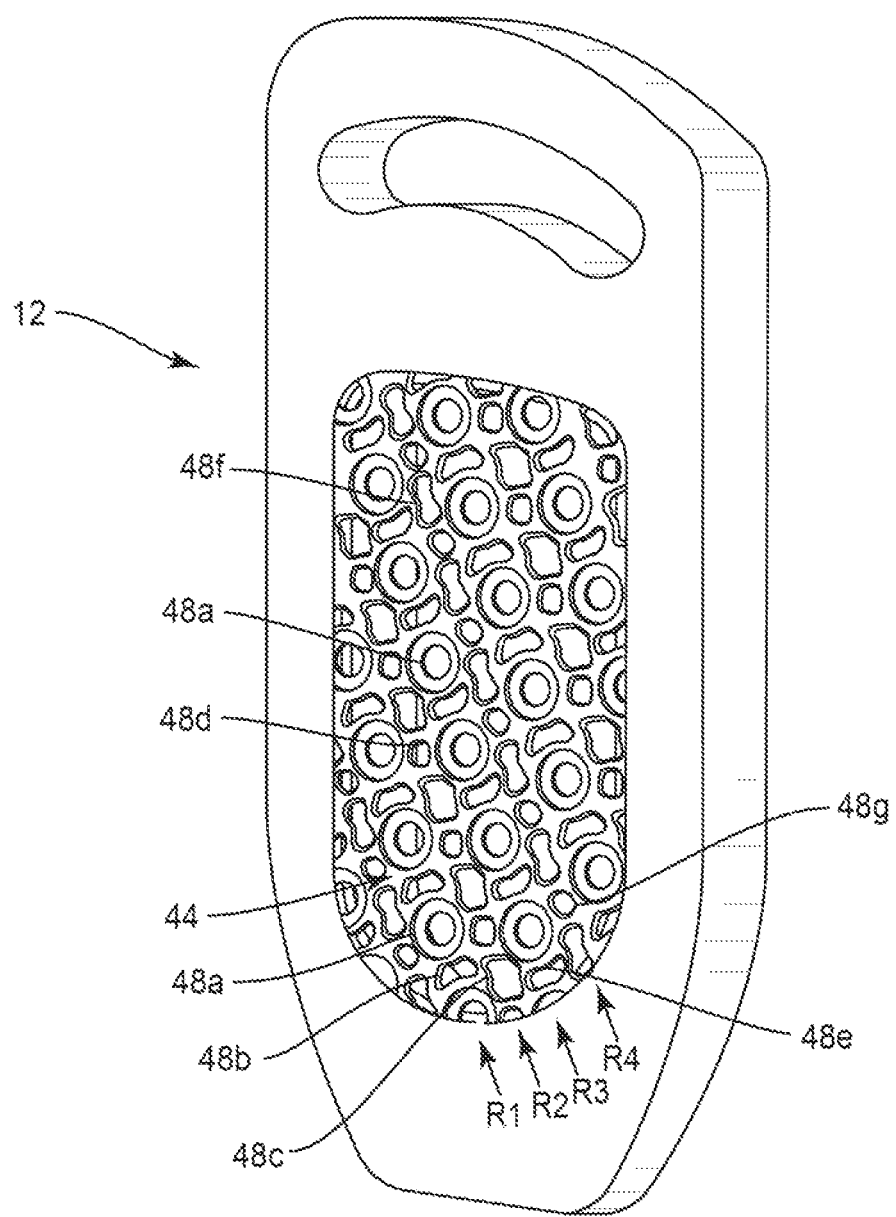
FIG. 5 is a perspective view of components of one embodiment of a spinal implant in accordance with the principles of the present disclosure.
Figure 8:
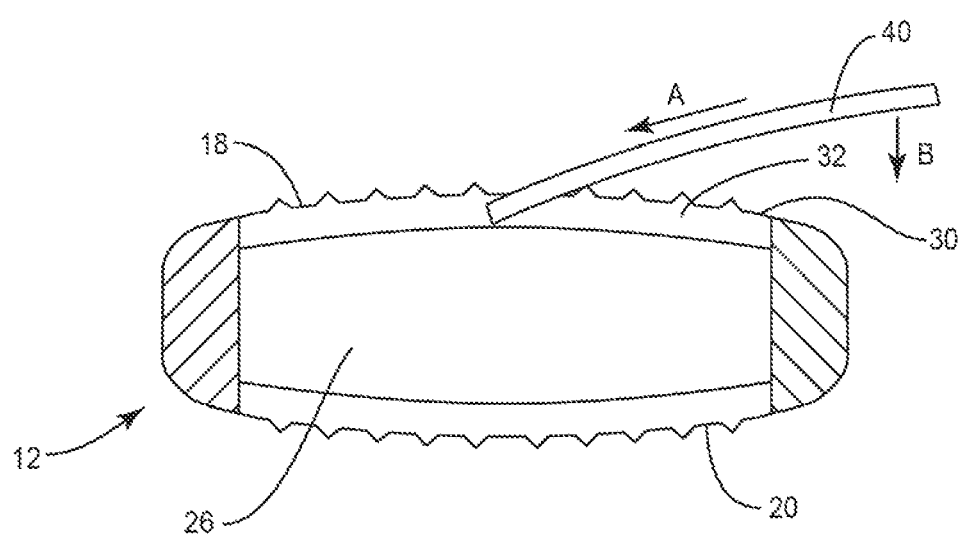
FIG. 8 is a side view of components of one embodiment of a spinal implant in accordance with the principles of the present disclosure.

Endcap 40 is disposable between a first configuration such that endcap 40 is not connected with the implant body of implant 12, for example as shown in FIG. 4, and a second configuration such that endcap 40 is integrally connected and/or assembled with the implant body of implant 12, for example as shown in FIG. 5 or FIG. 8, to resist and/or prevent egress of bone graft, agents and/or other selected materials from cavity 26, as described herein. For example, as shown in FIG. 8, endcap 40 is manipulated, in the directions shown by arrows A and B, from the first configuration and translated in a sliding engagement with and relative to surface 22 for disposal with recess 32. Flange 33 engages flange 43 and flange 33a engages flange 43a to retain endcap 40 with surface 22 and within recess 32 in a fixed and/or locked orientation. In some embodiments, bone graft, agents and/or other selected materials can be packed into cavity 26. Endcap 40 resists and/or prevents egress of bone graft, agents and/or other selected materials from cavity 26 through opening 30, as described herein. In some embodiments, endcap 40 is resiliently deformable for connection and/or assembly with the implant body of implant 12, as described herein.

Implant 12 includes an interbody endcap 60, as shown in FIG. 1, similar to endcap 40. Endcap 60 is configured for connection and mating engagement with the surface that defines recess 36. Endcap 60 includes a wall having a thickness configured to permit bone growth therethough, as described herein. The wall of endcap 60 includes flanges configured for disposal within recess 36. Flanges 37, 37a engage the flanges of endcap 60 to retain endcap 60 with surface 22 and within recess 36 in a fixed and/or locked orientation.

Endcap 60 includes a surface 64, similar to surface 44 described herein, having a uniform configuration that resists and/or prevents egress of bone graft, agents and/or other selected materials from cavity 26 in an integrally connected and/or assembled configuration with the implant body of implant 12, as described herein. In one embodiment, surface 64 includes a series of selectively configured and dimensioned openings 66, similar to openings 46 described herein.

Figure 3:
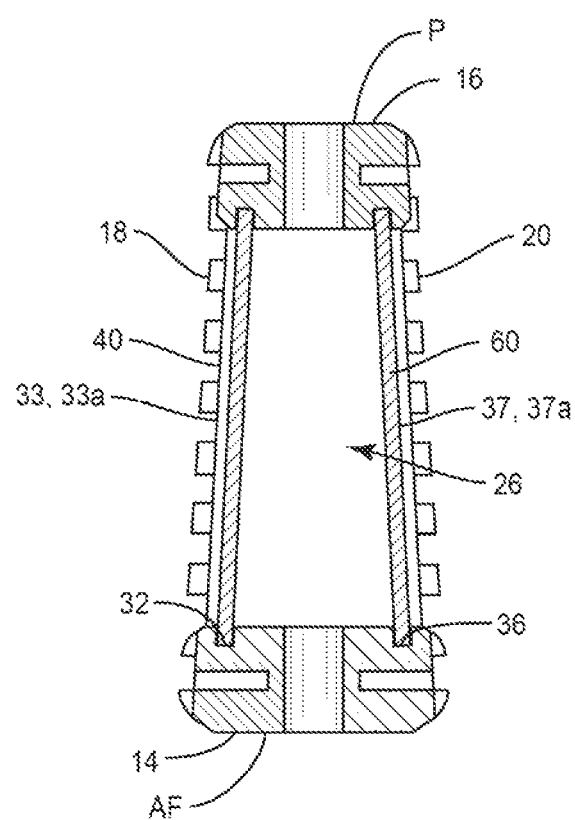
FIG. 3 is a cross section view of the components shown in FIG. 1.

Endcap 60 is disposable between a first configuration such that endcap 60 is not connected with the implant body of implant 12 and a second configuration such that endcap 60 is integrally connected and/or assembled with the implant body of implant 12, for example as shown in FIG. 1, to resist and/or prevent egress of bone graft, agents and/or other selected materials from cavity 26, similar to connection and/or assembly of endcap 40 with the implant body of implant 12. Endcap 60 is manipulated from the first configuration and translated in a sliding engagement with and relative to surface 22 for disposal with recess 36. Flanges 37, 37a engage the flanges of endcap 60 to retain endcap 60 with surface 22 and within recess 36 in a fixed and/or locked orientation. Endcaps 40, 60 are assembled with the implant body of implant 12, as shown in FIG. 3, to resist and/or prevent egress of bone graft, agents and/or other selected materials from cavity 26 through openings 30, 34. In some embodiments, endcap 40 or endcap 60 may be preformed with the implant body of implant 12.

In assembly, operation and use, system 10 including implant 12, similar to the systems and methods described with regard to FIGS. 1-8, is employed with a surgical procedure, such as, for example, for treatment of a spine of a patient including vertebrae V, as shown in FIGS. 6 and 7. System 10 may be employed with surgical procedures, such as, for example, discectomy, laminectomy, fusion, laminolomy, laminectomy, nerve root retraction, foramenotomy, facetectomy, decompression, spinal nucleus or disc replacement and bone graft and implantable prosthetics including plates, rods, and bone engaging fasteners for securement of implant 12 with vertebral tissue.

System 10 is employed for treatment of an applicable condition or injury of an affected section of a spinal column and adjacent areas within a body. For example, vertebrae V includes vertebrae V1, V2, which include diseased and/or damaged vertebrae and intervertebral discs. In some embodiments, implant 12 is configured for insertion within vertebral space S to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery and percutaneous surgical implantation, whereby vertebrae V is accessed through a mini-incision, or sleeve that provides a protected surgical pathway to the area. In some embodiments, once access to the surgical site is obtained, a partial or complete discectomy and/or corpectomy is performed for treating the spine disorder. The diseased and/or damaged portion of vertebrae V and diseased and/or damaged intervertebral discs are removed to create vertebral space S.

A preparation instrument (not shown) is employed to remove disc tissue, fluids, adjacent tissues and/or bone, and scrape and/or remove tissue from endplate surface E1 and/or endplate surface E2. In some embodiments, sequential trial implants are delivered along the surgical pathway and used to distract the intervertebral space and apply appropriate tension in the intervertebral space allowing for indirect decompression. In some embodiments, the size of implant 12 is selected after trialing, implant 12 is visualized by fluoroscopy and oriented before malleting into the intervertebral space.

Endcaps 40, 60 are assembled with the implant body of implant 12 and bone graft, agents and/or other selected materials are packed with cavity 26, as described herein. Endcaps 40, 60 resist and/or prevent egress of bone graft, agents and/or other selected materials from cavity 26 through surfaces 44, 64, for example, during introduction, delivery and/or insertion of implant 12 into vertebral space S and/or to contain bone graft, agents and/or other selected materials packed with cavity 26 until the interbody implant is implanted into vertebral space S such that openings 46, 66 allow bone growth therethrough upon disposal of implant 12 with tissue, as described herein.

An inserter is connected with a guide to direct implant 12 through the incision along the surgical pathway adjacent to a surgical site for implantation into space S. Implant 12 is delivered into the prepared space S between vertebra V1 and vertebra V2. Implant 12 is manipulated such that surface 18 engages endplate surface E1 and surface 20 engages endplate surface E2. Implant 12 engages and spaces apart opposing endplate surfaces E1, E2 and is secured within vertebral space S to stabilize and immobilize portions of vertebrae V. Endcaps 40, 60 permit bone growth therethough in connection with bone growth for fusion and fixation of vertebrae V1, V2, as described herein. Fixation of implant 12 with endplate surfaces E1, E2 may be facilitated by the resistance provided by the joint space and/or engagement with endplate surfaces E1, E2.

In some embodiments, implant 12 may engage only one vertebral endplate. In some embodiments, an agent(s), as described herein, may be applied to areas of the surgical site to promote bone growth. Components of system 10 including implant 12 can be delivered or implanted as a pre-assembled device or can be assembled in situ. Components of system 10 including implant 12 may be completely or partially revised, removed or replaced in situ. In some embodiments, one or all of the components of system 10 can be delivered to the surgical site via mechanical manipulation and/or a free hand technique.

In one embodiment, implant 12 may include fastening elements, which may include a locking structure, configured to facilitate fixation with vertebrae V1, V2 to secure joint surfaces and provide complementary stabilization and immobilization to a vertebral region. In some embodiments, the locking structure may include fastening elements such as, for example, rods, plates, clips, hooks, adhesives and/or flanges. In some embodiments, system 10 can be used with screws to enhance fixation. In some embodiments, system 10 and any screws and attachments may be coated with an agent, similar to those described herein, for enhanced bony fixation to a treated area. The components of system 10 can be made of radiolucent materials such as polymers. Radio-markers may be included for identification under x-ray, fluoroscopy, CT or other imaging techniques.

In one embodiment, system 10 includes a plurality of implants 12. In some embodiments, employing a plurality of implants 12 can optimize the amount vertebral space S can be spaced apart such that the joint spacing dimension can be preselected. The plurality of implants 12 can be oriented in a side by side engagement, spaced apart and/or staggered.

In some embodiments, the use of surgical navigation, microsurgical and image guided technologies may be employed to access, view and repair spinal deterioration or damage, with the aid of system 10. Upon completion of the procedure, the non-implanted components, surgical instruments and assemblies of system 10 are removed and the incision is closed.

Figure 9:
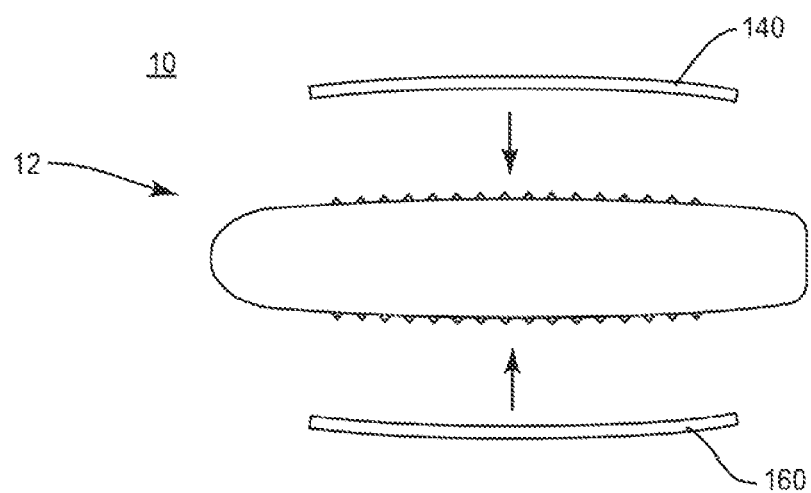
FIG. 9 is a side view of components of one embodiment of a spinal implant in accordance with the principles of the present disclosure with parts separated.
Figure 10:
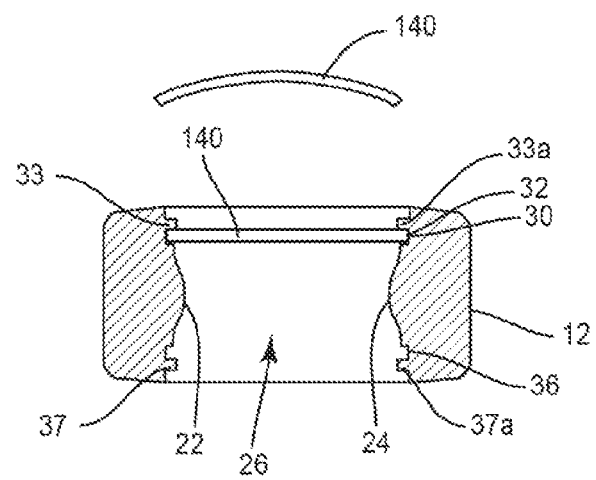
FIG. 10 is a side view of the components shown in FIG. 9.
Figure 11:
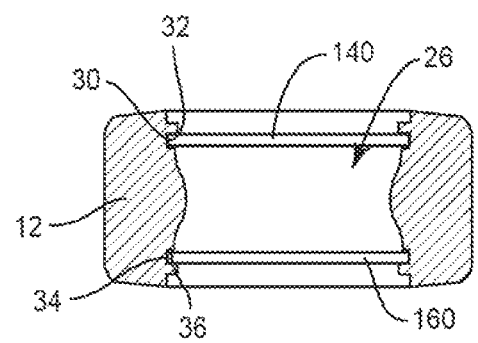
FIG. 11 is a side view of the components shown in FIG. 9.

In one embodiment, as shown in FIGS. 9-11, system 10, similar to the systems and methods described with regard to FIGS. 1-8, comprises implant 12, described herein, which includes an endcap 140, similar to endcaps 40, 60 described herein.

Endcap 140 is resiliently deformable and disposable between a first, expanded configuration such that endcap 140 is oriented in a substantially flat or even configuration, as shown in FIG. 9, and a second, contracted configuration such that endcap 140 is compressed, as shown in FIG. 10. This configuration of endcap 140 facilitates disposal with the implant body of implant 12, as described herein, in an integrally connected and/or assembled configuration with the implant body of implant 12 to resist and/or prevent egress of bone graft, agents and/or other selected materials from cavity 26, as described herein.

In some embodiments, one or more of the endcaps, as described herein, may have a semi-rigid, rigid, flexible or elastic configuration, and/or have elastic and/or flexible properties such as the elastic and/or flexible properties corresponding to the material examples described above such that the endcap provides a selective amount of expansion and/or extension. In some embodiments, the endcap can include a plurality of separately attachable or connectable portions or sections, or may be monolithically formed as a single continuous element.

Endcap 140 is manipulated from the expanded configuration and flexibly compressed to the contracted configuration. Endcap 140 is biased to the expanded configuration and released such that flanges, as described herein, of endcap 140 expand for disposal with recess 32. Flanges 33, 33a engage the flanges of endcap 140 to retain endcap 140 with surface 22 and within recess 32 in a fixed and/or locked orientation. Bone graft, agents and/or other selected materials can be packed into cavity 26. Endcap 140 resists and/or prevents egress of bone graft, agents and/or other selected materials from cavity 26 through opening 30, as described herein.

Implant 12, as shown in FIG. 9, includes an endcap 160, similar to endcap 140, which is resiliently deformable. Endcap 160 is disposable between a first, expanded configuration such that endcap 160 is oriented in a substantially flat or even configuration and a second, contracted configuration such that endcap 160 is compressed. Endcap 160 is manipulated from the expanded configuration and flexibly compressed to the contracted configuration. Endcap 160 is biased to the expanded configuration and released such that flanges, as described herein, of endcap 160 expand for disposal with recess 36. Flanges 37, 37a engage the flanges of endcap 160 to retain endcap 160 with surface 22 and within recess 36 in a fixed and/or locked orientation. Endcaps 140, 160 are assembled with the implant body of implant 12 to resist and/or prevent egress of bone graft, agents and/or other selected materials from cavity 26 through openings 30, 34, as described herein.

Figure 12:
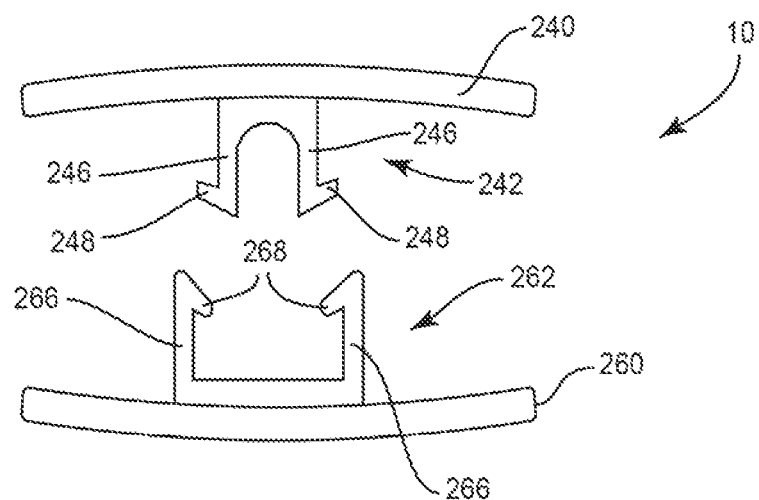
FIG. 12 is a side view of components of one embodiment of a spinal implant in accordance with the principles of the present disclosure.
Figure 13:
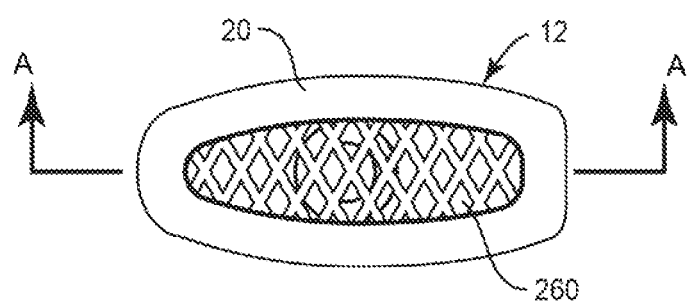
FIG. 13 is a top view of components of one embodiment of a spinal implant in accordance with the principles of the present disclosure.
Figure 14:
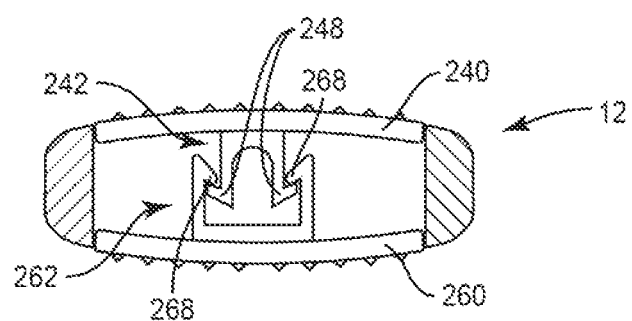
FIG. 14 is a side cross section view taken along lines A-A of the components shown in FIG. 13.

In one embodiment, as shown in FIGS. 12-14, system 10, similar to the systems and methods described herein, comprises implant 12, described herein, which includes endcaps 240, 260, similar to the endcaps described herein. Endcap 240 includes a mating part 242 and endcap 260 includes a mating part 262. Mating part 242 includes a relatively movable member, such as, for example, a pair of resiliently biased fingers 246 lockable with a pair of resiliently biased fingers 266 of mating part 262. Fingers 246 each include a barb 248 that are engageable with barbs 268 of fingers 266 to lock endcap 240 with endcap 260 in an integral connection and assembly with the implant body of implant 12. In some embodiments, endcaps 240, 260 are engageable in a snap fit connection for integral connection and assembly with the implant body of implant 12.

Endcap 240 or endcap 260 can be disposed for connection and assembly with the implant body of implant 12 such that the fingers extend into cavity 26. For example, endcap 240 can be fit with opening 30. Bone graft, an agent and/or other selected materials can be packed with cavity 26. Endcap 260 is disposed with and fit with opening 34. Fingers 246, 266 extend from endcaps 240, 260 into cavity 26. Barbs 248 engage barbs 268 such that fingers 246 deflect about fingers 266. Fingers 246 are biased such that barbs 248 are locked with barbs 268 and endcaps 240, 260 are locked in assembly with the implant body of implant 12. In some embodiments, endcap 240 or endcap 260 may be preformed with the implant body of implant 12 for locking engagement with the remaining endcap.

It will be understood that various modifications may be made to the embodiments disclosed herein. Therefore, the above description should not be construed as limiting, but merely as exemplification of the various embodiments. Those skied in the art will envision other modifications within the scope and spirit of the claims appended hereto.

What is claimed is:

1. An interbody implant comprising:
   a body comprising opposite top and bottom surfaces that are each configured to engage a vertebra, the body including an inner surface defining a cavity, the cavity including a first opening that extends through the top surface and a second opening that extends through the bottom surface; and
   at least one member positioned within one of the openings so as to block a portion of one of the openings, the at least one member having a thickness that permits bone growth therethrough and a surface configuration that resists and/or prevents egress of bone graft from the cavity,
   wherein the inner surface defines a recess that extends about the cavity, the recess including linear and arcuate portions, the at least one member being disposed in the recess.

2. An interbody implant as recited in claim 1, wherein the at least one member includes a perimeter and the body includes a flange that overlaps the perimeter.

3. An interbody implant as recited in claim 1, wherein the at least one member includes a perimeter that engages a slot of the body.

4. An interbody implant as recited in claim 1, wherein the at least one member is resiliently deformable.

5. An interbody implant as recited in claim 1, wherein the at least one member is resiliently deformable between a contracted configuration and an expanded configuration such that the at least one member is fixed with the body.

6. An interbody implant as recited in claim 1, wherein the surface configuration comprises mesh.

7. An interbody implant as recited in claim 1, wherein the surface configuration includes perforations.

8. An interbody implant as recited in claim 1, wherein the surface configuration comprises a series of selectively configured and dimensioned openings.

9. An interbody implant as recited in claim 1, wherein the surface configuration comprises a series of selectively configured and dimensioned sets of openings, wherein each set includes a plurality of alternately configured and dimensioned openings.

10. An interbody implant as recited in claim 1, wherein the at least one member comprises a first endcap member positioned in the first opening so as to block a portion of the first opening and a second endcap member positioned in the second opening so as to block a portion of the second opening, the end cap members each being positioned entirely between the top and bottom surfaces.

11. An interbody implant as recited in claim 1, wherein the at least one member comprises a first endcap member and the body includes a second endcap member.

12. A spinal implant comprising:
    an interbody implant extending between a first end and a second end, the ends extending between opposite top and bottom surfaces, an inner surface of the implant defining a cavity, the implant having a first opening that extends through the top and a second opening that extends through the bottom surface, the openings being in communication with the cavity;
    a first endcap member disposed in the first opening such that the first endcap member blocks a portion of the first opening; and
    a second endcap member disposed in the second opening such that the second endcap member blocks a portion of the second opening, each of the endcap members having a thickness that permits bone growth therethrough and a uniform surface configuration that resists and/or prevents egress of bone graft from the cavity,
    wherein the inner surface defines a recess that extends about the cavity, the recess including linear and arcuate portions, the first endcap member being disposed in the recess.

13. A spinal implant as recited in claim 12, wherein the first endcap member includes a perimeter and top end of the interbody implant that includes the top surface comprises a flange that overlaps the perimeter for disposal of the first endcap member with the top end.

14. A spinal implant as recited in claim 12, wherein the first endcap member is resiliently deformable between a first configuration and a second, expanded configuration such that the first endcap member is attachable with a top end of the interbody implant that includes the top surface, and the second endcap member is permanently fixed with a bottom end of the interbody implant that includes the bottom surface.

15. A spinal implant as recited in claim 12, wherein each of the uniform surfaces comprise a series of selectively configured and dimensioned openings.

16. An interbody implant comprising:

a body comprising opposite top and bottom surfaces that are each configured to engage a vertebra, the body including an inner surface defining a cavity, the cavity including a first opening that extends through the top surface and a second opening that extends through the bottom surface;

a first endcap member positioned within the first opening so as to block a portion of the first opening, the first endcap member comprising opposite first and second surfaces; and a second endcap member positioned within the second opening so as to block a portion of the second opening, the second endcap member comprising opposite first and second surfaces, the endcap members each having a thickness that permits bone growth therethrough and a surface configuration that resists and/or prevents egress of bone graft from the cavity, wherein the first endcap member includes a male mating part extending outwardly from the second surface of the first endcap member and the second endcap member includes a female mating part extending outwardly from the second surface of the second endcap member that engages the male mating part to couple the endcap members to one another.

17. An interbody implant as recited in claim 16, wherein the male mating part comprises spaced apart first fingers that each include a first barb and the female mating part comprises spaced apart second fingers that each include a second barb, the first barbs being configured to engage the second barbs such that the first fingers deflect about the second fingers.

18. An interbody implant as recited in claim 17, wherein the first fingers are biased such that the first barbs are locked with the second barbs.

19. An interbody implant as recited in claim 16, wherein the first surface of the first endcap member is aligned with the top surface and the first surface of the second endcap member is aligned with the bottom surface.

* * * * *